United States Patent
Harrold et al.

(10) Patent No.: US 8,666,481 B2
(45) Date of Patent: Mar. 4, 2014

(54) FETAL MOVEMENT MONITOR

(75) Inventors: Lewis Norman Harrold, Georgetown, MA (US); Anthony Ralph Diciaccio, Peabody, MA (US)

(73) Assignee: Analogic Corporation, Peabody, MA (US)

( * ) Notice: Subject to any disclaimer, the term of this patent is extended or adjusted under 35 U.S.C. 154(b) by 75 days.

(21) Appl. No.: 13/203,614

(22) PCT Filed: Feb. 27, 2009

(86) PCT No.: PCT/US2009/035457
§ 371 (c)(1), (2), (4) Date: Aug. 26, 2011

(87) PCT Pub. No.: WO2010/098767
PCT Pub. Date: Sep. 2, 2010

(65) Prior Publication Data
US 2011/0306893 A1 Dec. 15, 2011

(51) Int. Cl.
*A61B 5/0444* (2006.01)

(52) U.S. Cl.
USPC .......................................................... 600/511

(58) Field of Classification Search
USPC .................................................. 600/376, 511
See application file for complete search history.

(56) References Cited

U.S. PATENT DOCUMENTS

| | | | |
|---|---|---|---|
| 4,569,356 A | | 2/1986 | Kyozuka |
| 4,573,479 A | * | 3/1986 | Tuccillo .................. 600/511 |
| 4,781,200 A | * | 11/1988 | Baker ...................... 600/483 |
| 4,809,702 A | * | 3/1989 | Fabbri et al. ................ 600/453 |
| 4,898,179 A | * | 2/1990 | Sirota ....................... 600/483 |
| 4,951,680 A | | 8/1990 | Kirk et al. |
| 5,010,889 A | | 4/1991 | Bredesen et al. |
| 5,069,218 A | | 12/1991 | Ikeda |
| 5,088,497 A | | 2/1992 | Ikeda |
| 5,109,856 A | | 5/1992 | Bonnefous et al. |
| 5,123,420 A | | 6/1992 | Paret |
| 5,170,791 A | | 12/1992 | Boos et al. |
| 5,218,969 A | | 6/1993 | Bredesen et al. |
| 5,372,139 A | | 12/1994 | Holls et al. |
| 5,509,421 A | | 4/1996 | Muller et al. |
| 6,045,500 A | | 4/2000 | Bieniarz |
| 6,115,624 A | | 9/2000 | Lewis et al. |

(Continued)

FOREIGN PATENT DOCUMENTS

| | | |
|---|---|---|
| JP | H6/1994-296593 A | 10/1994 |
| JP | H10/1998-511015 | 10/1998 |
| WO | 2006/082977 A1 | 8/2006 |
| WO | 2008139372 A1 | 11/2008 |

OTHER PUBLICATIONS

Menscher, Corey, Kickbee has a New Home, 2008, pp. 1-2, No. XP-002553066, http://portfolio.menscher.com/itp/kickbee/.

(Continued)

*Primary Examiner* — Eric D. Bertram
(74) *Attorney, Agent, or Firm* — Driggs, Hogg, Daugherty & Del Zoppo Co. LPA

(57) ABSTRACT

A monitoring system includes a physiologic monitoring device (102) with an accelerometer (202) that senses fetal movements of a fetus in the womb of a human or animal patient and generates signals indicative thereof, a signal identifier (108) that identifies signals from the generated signals that correspond to a predetermined fetal movement, and a counter (112) that counts the identified signal.

32 Claims, 4 Drawing Sheets

(56) References Cited

U.S. PATENT DOCUMENTS

| | | |
|---|---|---|
| 6,454,716 B1 | 9/2002 | Zumeris |
| 6,662,043 B1 | 12/2003 | Shine |
| 6,751,498 B1 | 6/2004 | Greenberg |
| 6,984,208 B2 | 1/2006 | Zheng |
| 2006/0058650 A1* | 3/2006 | Sharony .................. 600/437 |
| 2007/0102501 A1* | 5/2007 | Nguyen .................. 235/1 R |
| 2008/0319353 A1* | 12/2008 | Howell et al. ................. 600/595 |
| 2010/0191154 A1* | 7/2010 | Berger et al. ................. 600/595 |
| 2010/0305481 A1* | 12/2010 | Igney et al. .................. 600/595 |

OTHER PUBLICATIONS

International search report for PCT/US09/35457, published as WO 2010/098767, Nov. 11, 2009.

First Office Action, JP 2011-552009, PCT/US2009/035457, Aug. 20, 2013.

* cited by examiner

FETAL MOVEMENT MONITOR

This application is a national filing of PCT application Ser. No. PCT/US09/35457, filed Feb. 27, 2009, published as WO2010/098767 on Sep. 2, 2010.

TECHNICAL FIELD

The following generally relates to identifying fetal movements of interest such as fetal kicks from a fetus in the womb of a human or animal patient. However, it also relates to identifying other fetal movements and/or movements of the patient carrying the fetus.

BACKGROUND

During labor, physiological parameters such as fetal heart rate are monitored in order to identify signs of fetal distress, or warn that the fetus may not be well or is becoming excessively fatigued. Prior to labor, the mother may undergo one or more ultrasound exams, which provide fetal heart rate and fetal size information that is used to identify markers of fetal growth during pregnancy. Unfortunately, ultrasound exams can be expensive and typically are performed only once during pregnancy. Historically, mothers sense fetal movements and midwives have the mother count those movements. A moving fetus is felt to be a healthy fetus. With the increasing age of mothers, there has been an increase in difficult pregnancies which would benefit from exams.

The literature indicates a correlation between fetal health and fetal kicks with less healthy fetuses often having fewer kicks relative to healthy fetuses. In one instance, the mother senses fetal movements and fills in a kick chart when she believes a sensed movement is a fetal kick. A kick chart is a form or graph used by a pregnant woman in the later stages of pregnancy to record the activity of her fetus. Another approach is to have the mother carry or wear a manually activated counter. With this approach, the mother increments the counter rather than filling in the chart.

In either instance, fetal kick activity over time can be determined from the recorded information. As such, the recorded information can be used to identify changes and trends in the kicks that occur in a given time interval. Unfortunately, the above approaches require the mother to sense and record kick events. In addition, the recorded information may not accurately reflect the fetus' kicks as the mother may not sense all kicks during a kick observation time interval, the mother may not record all sensed kicks, a sensed movement thought to be a fetal kick may be a different type of movement such as rolling around, a sensed movement thought not to be a fetal kick may in fact be a fetal kick, and the fetus may be sleeping when the mother is actively attempting to sense fetal movement.

SUMMARY

Aspects of the application address the above matters, and others.

In one aspect, a monitoring system includes a physiologic monitoring device with an accelerometer that senses fetal movements of a fetus in the womb of a human or animal patient and generates signals indicative thereof. The system further includes a signal identifier that identifies signals from the generated signals that correspond to a predetermined fetal movement. The system further includes a counter that counts the identified signal.

In another aspect, a method includes sensing a fetal movement of a fetus within the womb of a human or animal patient, generating a signal indicative of the sensed fetal movement, determining whether the signal corresponds to a fetal kick, and counting the signal in response to determining the signal corresponds to a fetal kick.

In another aspect, a monitoring apparatus includes a transducer that senses a physiologic movement indicative of fetal movement within the womb of a human or animal patient and generates signals indicative thereof, a physiologic signal identifier that identifies signals from the generated signals that correspond to a fetal kick, and a counter that counts the identified physiologic signal.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
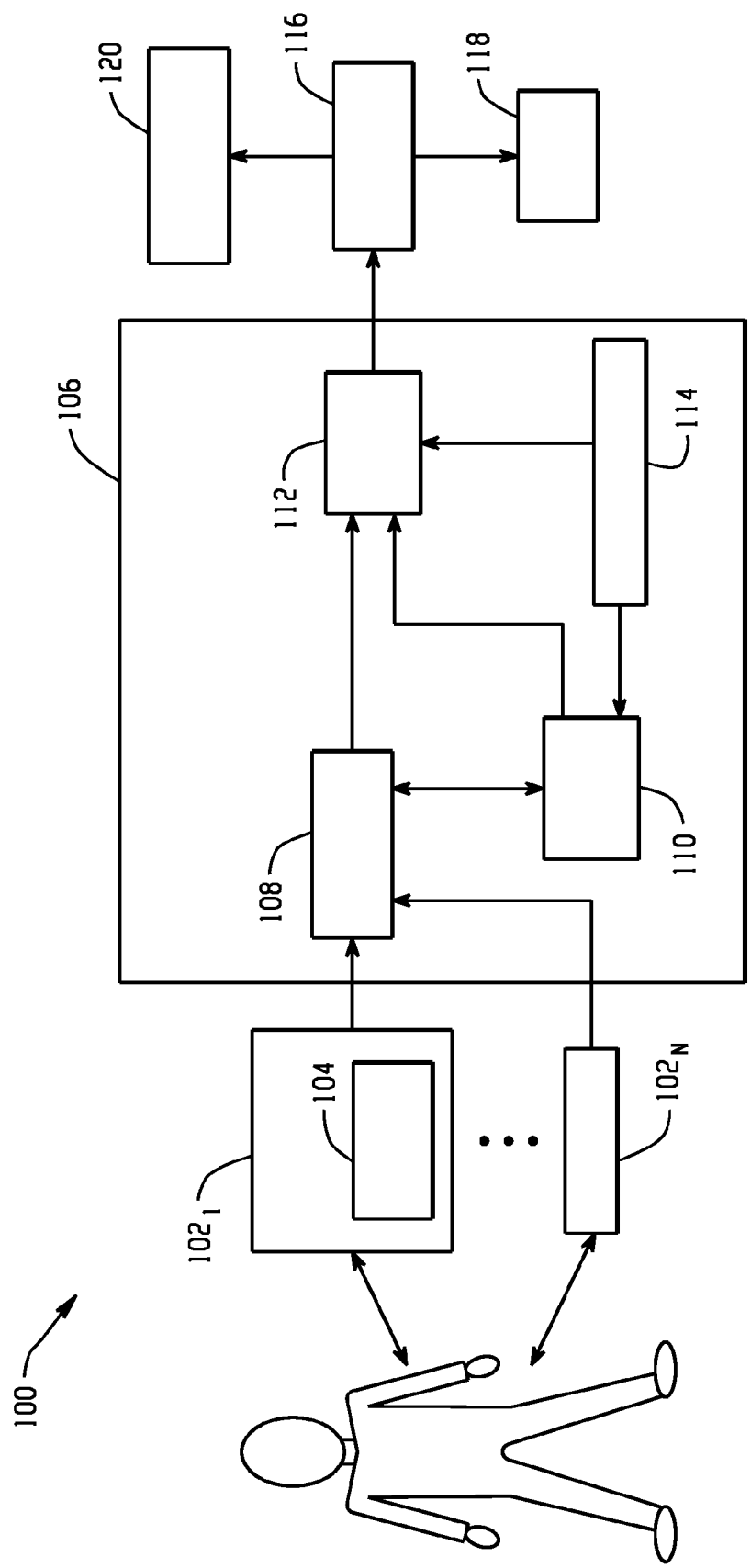
FIG. 1 illustrates an example monitoring system.

FIG. 1 illustrates an example monitoring system 100. The system 100 includes N physiologic monitoring devices or monitors $102_1$-$102_N$ (wherein N is an integer equal to or greater than one), collectively referred to herein as monitoring devices 102. The monitoring devices 102 are configured to monitor activity such as fetal kicks, fetal heart rate, fetal heart cycle, and/or other fetal activity in the womb of a pregnant human or animal patient and/or activity of the patient. As described in greater detail below, at least one of the monitors 102 (the monitor $102_1$ in the illustrated example) includes a movement sensor 104 such as a transducer configured to sense activity, such as a physiologic movement, and generate a signal indicative thereof.

A processing device 106 processes signals generated by the monitors 102. The illustrated processing device 106 includes a signal identifier 108 that identifies signals generated by the movement sensor 104 that correspond to particular activity of interest such as fetal kicks and/or other activity of interest. As described in greater detail below, in one instance this includes evaluating one or more characteristics of the signals generated by the movement sensor 104 such as frequency, power spectrum, periodicity, origin and/or other characteristic, and identifying signals of interest based on predetermined frequency and/or power spectrum ranges, a predefined periodicity, and/or a reference origin. Other information such as a signal indicative of fetal heart rate can additionally be used to facilitate identifying signals of interest.

Identified signals of interest or information about such signals can be stored in storage 110 and/or further processed. A signal not identified as being a signal of interest or information about such signals can also be stored in the storage 110 and/or further processed, or discarded, ignored, and/or otherwise processed. Other information can also be stored the storage 110. For example, learned patterns of fetal motion and/or other information can also be stored in the storage 110. Such information can also be utilized when processing sensed signals.

A counter 112 counts identified signals of interest, or increments a count value for identified signal of interest, and generates an output signal indicative thereof. In the context of fetal kick counting, this allows for counting of fetal kicks without requiring the mother to manually identify, count and record kicks. A timing apparatus such as a clock 114 can be used to timestamp or generate timing indicia for the individual or groups of identified signals of interest. Additionally or alternatively, the clock 114 can be used to count identified signals during one or more predetermined time intervals. For example, in one instance the clock 114 is used to count identified signals during consecutive non-overlapping time intervals, overlapping time intervals, and/or time intervals separated in time such as seconds, minutes, hours, days, weeks, months, etc.

A metric determiner 116 determines a metric such as a fetal health metric based on the output of the processing device 106. As described in greater detail below, this may include generating a metric based on a change in the number of identified signals for a given time interval for a plurality of such time intervals, the total number of identified signals in a given time period, and/or otherwise. When identifying fetal kicks, for example, such a metric can be used to determine a health of the fetus, such as determining whether the number of kicks per time interval increases, remains about the same or decreases, is greater than a first predetermined threshold value, is less than a second predetermined threshold value, "learned" pattern of fetal activity, etc. Such information can be used to facilitate determining whether a fetus is likely to be in distress.

In the illustrated example, the system 100 further includes or is in communication with an output device 118 such as a display, a portable storage medium, a network communications interface, and/or other output device. The number of counts, the number of counts as a function of time, the generated metric, and/or other information can be presented audibly and/or visually (e.g., on a liquid crystal, seven segment or other display, via a light emitting diode pattern and/or color, etc.), and/or transferred to another system via the portable storage medium or the network communications interface.

The illustrated example also includes a notification component 120 that selectively conveys a notification based on predetermined criteria, learned fetal motion pattern(s), and/or otherwise. The learned fetal motion pattern can be stored and compared with current information on an hourly, daily, weekly, monthly, or other basis. With fetal kick counting, the notification component 120 can be configured to send a notification when the number of kicks per time decreases over time by a value greater than a given threshold value. Such a notification may include the number of kicks as a function of time, the decrease in the number of kicks, indicia indicating such information, and/or other information. The notification may be a signal sent to a pager, an email message sent to an email account, a text message sent to a cell phone, a voice message sent to a telephone, and/or notification. In another embodiment, the notification component 120 is omitted.

Figure 2:
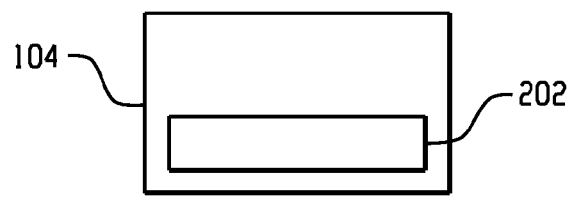
FIG. 2 illustrates an example movement sensor.

FIG. 2 illustrates an embodiment in which the movement sensor 104 of FIG. 1 includes an accelerometer 202. The illustrated accelerometer 202 is a multi-axis accelerometer and senses movement, including the magnitude and direction of the movement. Such an accelerometer allows for monitoring fetal movement such as fetal kicks and/or a representation of an approximate three dimensional (3D) location of the fetus in the womb. The three dimensional location may facilitate distinguishing kicks and/or other activity between fetuses when more than one fetus is in the womb. In another instance, a single axis accelerometer is used.

The accelerometer 202 is selectively placed on the subject, for example, over the fetus in the womb. In one instance, a signal indicative of the fetal heart beat is used to facilitate placement of the accelerometer 202 on the subject. For example, where the signal is an audio signal or pattern of varying light intensity, the relative intensity or loudness of the audio signal can facilitate identifying the location of the fetus in the womb. In another instance, the signal may be an ultrasound signal used to generate a two or three dimensional graphical representation which can be used to facilitate determining the location of the fetus in the womb. In yet another embodiment, an anatomical model, historical information about other patients, and/or other information is used to facilitate suitably placing the accelerometer 202 on the body.

Figure 3:
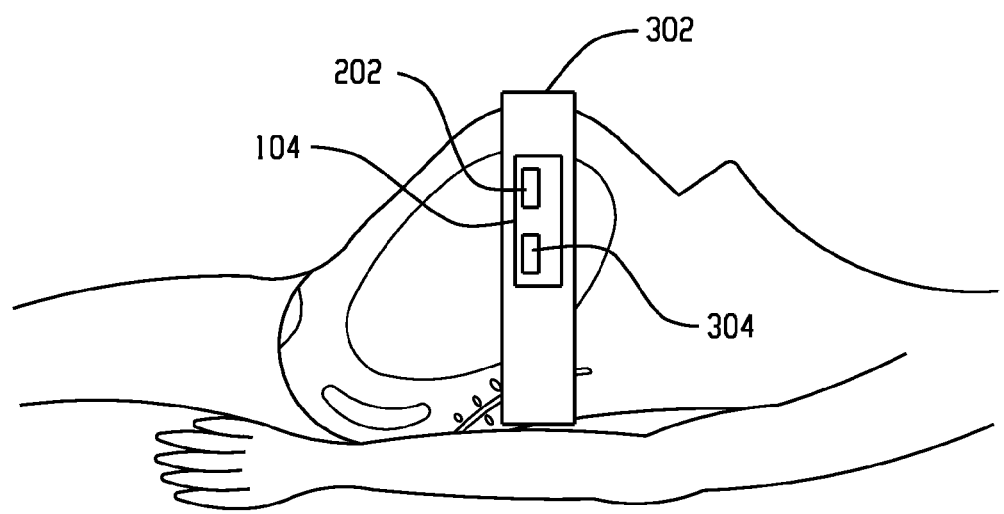
FIGS. 3-5 illustrate various carriers for carrying the movement sensor.

In one embodiment, the accelerometer 202 is carried by and held in position on the subject by a carrier such as a flexible belt, strap or the like configured to surround the body at the abdomen. In this instance, the accelerometer 202 may be removeably affixed to the carrier or part of the carrier. The carrier may include a stretchable material so as to be capable of expanding and contracting to conform to the size and shape of the subject. In another instance, the carrier may include one or more fasteners such as a hook and loop fastener, a button, a snap, a pin, and/or other fastener. An example of such a carrier is shown in FIG. 3, which shows a strap 302 with the movement sensor 104 affixed thereto. Electronics 304 include a communications interface for conveying the signal generated by the accelerometer 202 via cable or wirelessly. In another embodiment, the electronics 304 are located on the strap 302, outside of the movement sensor 104.

Figure 4:
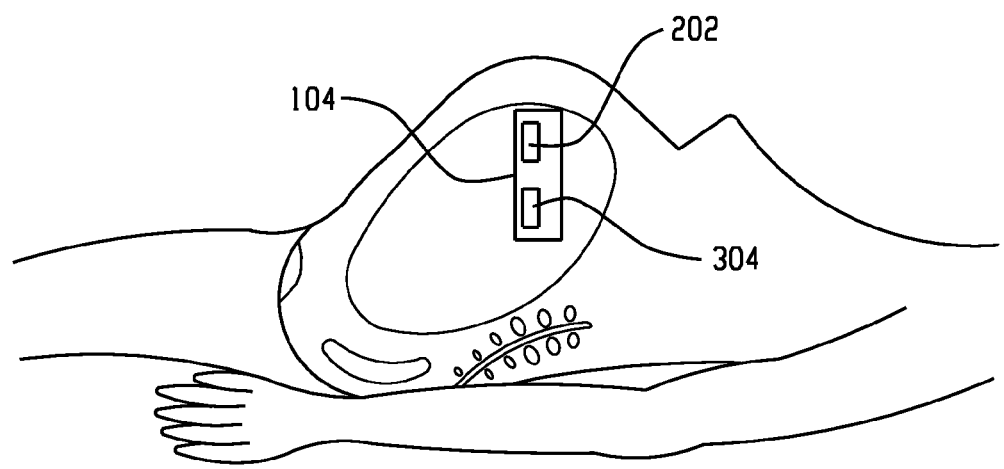

In another embodiment, the movement sensor 104 includes a surface with a bio-adhesive material for temporarily affixing the movement sensor 104 to the skin of the subject. This is shown in connection with FIG. 4.

Figure 5:
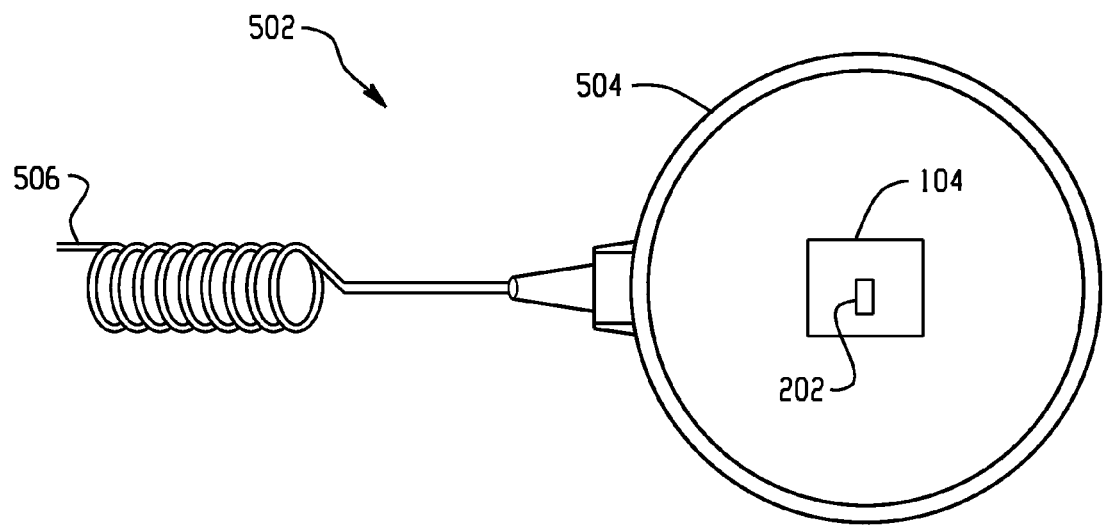

In yet another instance, the movement sensor 104 may be part of or work in conjunction with another device such as a fetal heart monitor or tococardiograph belt. As shown in connection with FIG. 5, such a device 502 may include an ultrasound transducer 504, which senses signals indicative of the fetal heart rate, and a cable 506 for conveying sensed signals to a processor. The resulting ultrasound data may be used to facilitate placement of the accelerometer 202 on the patient and/or maintaining suitable placement on the patient as the fetus may move around. An example of such a device is described in greater detail in U.S. Pat. No. 5,509,421, filed on Apr. 25, 1995, and entitled "System, With Sensor Positioning Indicator, For Monitoring A Biological Signal," the entirety of which is incorporated herein by reference.

Figure 6:
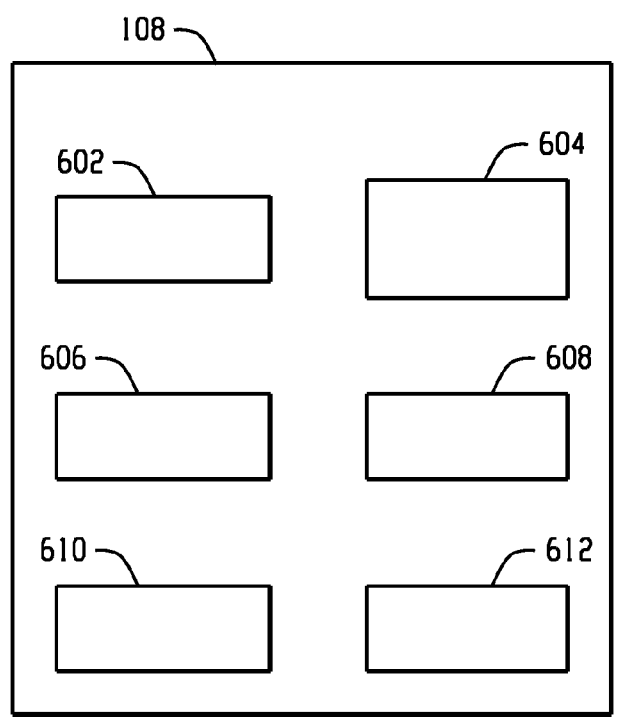
FIG. 6 illustrates an example signal identifier.

FIG. 6 illustrates a non-limiting embodiment of the signal identifier 108 of FIG. 1. For explanatory purposes, the following discusses the signal identifier 108 in connection with monitoring fetal kicks of a fetus in the womb of a patient, and is not limiting.

In the illustrated embodiment, the signal identifier 108 includes a frequency determiner 602 that determines a frequency of the signals from the movement sensor 104, a power spectrum determiner 604 that determines power spectral information of the signals from the movement sensor 104, a periodicity determiner 606 that determines whether signals from the movement sensor 104 are periodic or aperiodic, which in one non-limiting instance refers to a signal that does not repeat its values or shape in regular intervals or periods, and an origin determiner 608 that estimates an approximate physical origin of the signal from the movement sensor 104 in the patient.

The signal identifier 108 further includes a decision component 610. The illustrated decision component 610 includes a filter that is configured to substantially only pass signals having a frequency and an energy within predetermined frequency and energy ranges, a periodicity substantially similar to a predetermined periodicity of interest, and an origin that substantially aligns with an approximated reference origin. In another embodiment, the filter is configured to substantially pass signals based on a sub-combination (one or more but less than all) of the frequency, energy, periodicity or origin information. For example, in another instance the filter identifies and passes signals based on a frequency and energy. In this instance, periodicity and/or origin information can be used to confirm, validate, or verify identification of signals of interest. Other combinations are also contemplated herein. The filter can employ analog, digital and/or other suitable signal processing techniques.

In another embodiment, the decision component 610 determines whether to pass a signal based on a set of rules and the frequency, energy, periodicity, origin and/or other information. This includes, and is not limited to, fuzzy logic, neural networks, probabilities, inferences, cost functions, classifiers (implicitly and/or explicitly trained), and the like. Other approaches are also contemplated herein. The decision component 610 may also correlate signals, such as sensed signals with fetal heart rate or other fetal physiologic signals. Such information can also be used by the decision component 610 to identify signals.

A noise canceller 612 cancels background noise, non-biological function signals, repetitive signals, signals corresponding to the subject rather than the fetus, and/or other known signals that are not indicative of the signal to be identified. The noise canceller 612 can be omitted in various embodiments.

It is to be appreciated that one or more of the frequency determiner 602, the power spectrum determiner 604, the periodicity determiner 606, or the origin determiner 608 are omitted in other embodiments.

Generally, the frequency of fetal kicks is lower than the frequency of biological functions and physical activity. For instance, the literature indicates that a healthy fetus will kick on average about five (5) times per hour, which corresponds to a frequency of about 0.0014 Hz, when awake and moving in the womb, whereas the frequency of the heart cycle and the respiratory cycle respectively are in the range of about 0.5-5.0 Hz and 0.05-2.5 Hz, and the frequency of walking is about 2 Hz. Such a difference in frequency allows for distinguishing, based on frequency, signals indicative of fetal kicks from signals indicative of other fetal or mother heart or respiratory activity, a walking mother, and/or other non-fetal kick activity. This allows for configuring the decision component 610 based on a suitable cut off frequency(s), which can be based on a predetermined frequency range that corresponds to a frequency band of interest, such as a band corresponding to fetal kicks. As such, the decision component 610 can identify signals of interest and/or signals not of interest based on signal frequency.

Further, a signal indicative of a fetal kick generally is higher in energy relative to a signal indicative of a biological function (e.g., heart beat, respiration, etc.) and physical activity (e.g., walking, etc.). This allows for distinguishing, based on energy, signals indicative of fetal kicks from signals indicative of such and/or other biological functions and physical activity. As such, in one embodiment the decision component 610 makes decisions based on determined energy and a predetermined energy range corresponding to an energy of interest such as an energy corresponding to fetal kicks. As such, in one embodiment the decision component 610 identifies signals of interest and/or other signals based on signal energy.

Further, the energy peaks of the signals indicative of the fetal kicks generally occur randomly, whereas energy peaks for rhythmic biological functions (e.g., heart beat, respiration, etc.) generally occur with some periodicity. This allows for distinguishing, based on periodicity, signals indicative of fetal kicks from signals indicative of rhythmic biological functions and physical activity. As such, in one embodiment the decision component 610 is configured to make decisions based on the determined periodicity of the signals with a predetermined periodicity of interest such as a periodicity corresponding to fetal kicks. As such, the decision component 610 can be configured to identify signals of interest and/or signals not of interest based on signal periodicity. As one or more of the energy peaks may occur with some period, the signal identifier 108 can be configured to employ the periodicity information as supplemental information to validate the identification of a signal of interest by the frequency determiner 602 and/or the power spectrum determiner 604.

Further, the origin of the signals provides information that facilitates determining whether the signals correspond to the fetus or another source. By way of example, signals with origins at or near the location of the fetus are more likely to correspond to the fetus, whereas signals with origins relatively farther away from the location of the fetus are less likely to come from the fetus. As such, in one embodiment the decision component 610 can be configured to make decisions based on the determined origin of a signal with a location of the fetus, which can be estimated based on a fetal heart signal, an ultrasound signal and/or other signal indicative of the location of the fetus in the womb.

Figure 7:
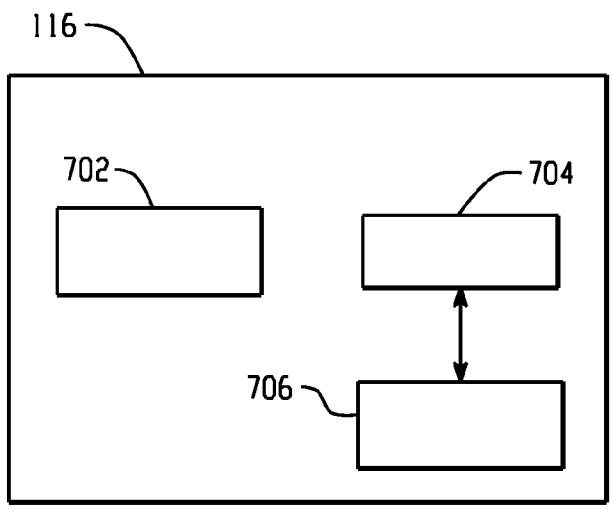
FIG. 7 illustrates an example metric determiner.

FIG. 7 illustrates a non-limiting embodiment of the metric determiner 116 of FIG. 1. The illustrated metric determiner 116 includes a pattern determiner 702 and a classifier 704. With respect to fetal kick monitoring, the pattern determiner 702 determines a kick pattern as a function of time based on the output of the processing component 106 of FIG. 1. For example, in one instance the pattern determiner 702 determines a number of kicks in a given time interval for a plurality of different time intervals which are separated in time.

The classifier 704 classifies patterns based on one or more known and/or learned patterns, such as patterns in a pattern bank 706. In one instance, the pattern bank 706 includes known kick patterns corresponding to fetal distress and known kick patterns corresponding to absence of fetal distress patterns. In this instance, the classifier 704 classifies the determined pattern based on the known patterns. Additionally or alternatively, the classifier 704 may use rules, fuzzy logic, neural networks, thresholds, probabilities, cost functions, inferences, and/or the like to classify the determined pattern based on the predetermined patterns. The output of the metric determiner 116 provides a fetal health metric.

In another embodiment, the metric determiner 116 compares the kick pattern as a function of time with a predetermined threshold value, and the result provides the fetal health metric.

Figure 8:
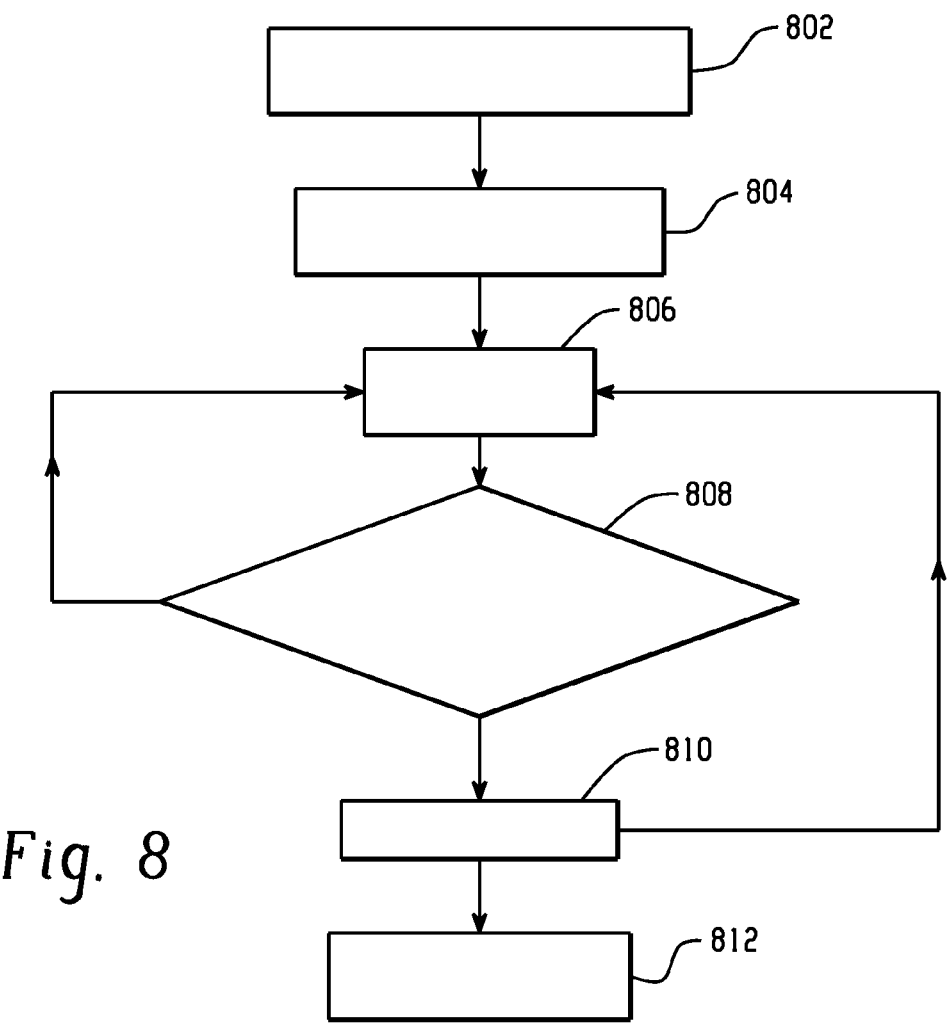
FIG. 8 illustrates an example method.

FIG. 8 illustrates a method for monitoring movement such as fetal kicks.

At 802, a fetal movement sensor 104 is suitably positioned on the womb over the fetus. Fetal heart rate, ultrasound data, and/or other information can be used to facilitate suitable placement of the sensor on the womb. In one instance, the sensor can be an accelerometer 202, as described herein.

At 804, a fetal movement of interest selected. As described herein, in one instance the fetal movement corresponds to a fetal kick.

At 806, a fetal movement is sensed by the fetal movement sensor 104.

At 808, it is determined whether the sensed fetal movement corresponds to the fetal movement of interest. As discussed herein, this may include analyzing the frequency, the power spectrum, the periodicity, and/or the origin of the sensed fetal movement, other information about the sensed fetal movement such as a fetal heart cycle, a fetal hear rate, etc., and/or other information.

If the sensed fetal movement corresponds to the fetal movement of interest, then at 810 a count value is incremented. Otherwise, the count value is not incremented. Acts 806 to 810 can be repeated for a given time interval for one or more such time intervals.

At 812, a fetal health metric is generated based on the count value(s).

The above may be implemented by way of computer readable instructions, which when executed by a computer processor(s), cause the processor(s) to carry out the described techniques. In such a case, the instructions can be stored in a computer readable storage medium associated with or otherwise accessible to the relevant computer. Moreover, the processing component 106 and metric determiner 116 can be implemented via software and/or hardware.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A monitoring system, comprising:
  a physiologic monitoring device with an accelerometer that senses fetal movements of a fetus in the womb of a human or animal mother and generates signals indicative thereof;
  a signal origin determiner that determines origins of the fetal movements in the patient based on the generated signals;
  a signal identifier that identifies signals from the generated signals that correspond to a predetermined fetal movement, wherein the signal identifier validates an identified signal based on the determined origin; and
  a counter that counts the identified signal.

2. The apparatus of claim 1, wherein the predetermined fetal movement is a fetal kick.

3. The apparatus of claim 1, wherein the accelerometer senses a physiologic movement of the mother that corresponds to the fetal movements.

4. The apparatus of claim 1, wherein the accelerometer affixes to the patient via one of a belt, strap, adhesive or heart activity monitoring device.

5. The apparatus of claim 4, wherein the accelerometer is positioned over the womb based on an estimate of a fetus location in the womb, which is based on a fetal heart rate.

6. The apparatus of claim 1, wherein the signal identifier identifies signals based on one or more predetermined signal characteristics.

7. The apparatus of claim 1, further comprising a frequency determiner that determines frequencies of the generated signals, wherein the signal identifier identifies signals having frequencies in a predetermined frequency range, which correspond to a frequency of the fetal movement of interest.

8. The apparatus of claim 1, further comprising a power spectrum determiner that determines power spectral information about the signals, wherein the signal identifier identifies signals having power spectrums in a predetermined power spectrum range, which correspond to a power spectrum of the fetal movement of interest.

9. The apparatus of any of claims 7 to 8, further comprising a periodicity determiner that determines a periodicity of the generated signals, wherein the signal identifier validates an identified signal based on the determined periodicity.

10. The apparatus of claim 1, wherein the signal identifier identifies signals based on one or more predetermined rules.

11. The apparatus of claim 1, further including a timing apparatus that provides at least one of a time stamp of an identified signal or a time interval in which the counter counts the identified signals.

12. The apparatus of claim 1, further including an output device, wherein a count value is presented via the output device.

13. The apparatus of claims 1, further including a metric determiner that determines a fetal health metric based on a count value.

14. The apparatus of claim 1, further including a metric determiner that determines a fetal health metric based on a change in a count value over time.

15. The apparatus of claim 1, further including a metric determiner that determines a fetal health metric based on at least one of predetermined criteria or a learned fetal motion pattern.

16. The apparatus of claim 1, further including a notification component that selectively conveys a signal indicative of a health of the fetus.

17. The apparatus of claim 16, wherein the signal is indicative of one or more of a number of fetal kicks for a given time interval or a change in a number of fetal kicks in different time intervals.

18. The apparatus of claim 1, further comprising:
  a pattern determiner that determines a fetal kick pattern; and
  a classifier that classifies the fetal kick pattern.

19. The apparatus of claim 18, wherein the classifier classifies the kick pattern as indicative of fetal distress.

20. The monitoring system of claim 1, wherein the sensed fetal movements include fetal kicks and non-fetal kicks, the predetermined fetal movement is a fetal kick, and the signal identifier only identifies the signals from the generated signals that correspond to the fetal kicks.

21. A method, comprising:
  sensing, by a physiological monitoring device, a fetal movement of a fetus within the womb of a human or animal patient;
  generating a signal indicative of the sensed fetal movement;
  determining a frequency of the signal;
  identifying the signal as a fetal kick when the determined frequency is within a predetermined frequency range corresponding to a fetal kick
  determining an origin of the signal in the womb;
  determining a location of the fetus in the womb:
  validating the signal as a fetal kick when the origin corresponds to the determined location: and
  counting the signal in response to determining the signal corresponds to a fetal kick.

22. The method of claim 21, wherein the fetal movement is sensed with an accelerometer disposed on the patient.

23. The method of claim 22, further including positioning the accelerometer on the patient based on a fetal heart rate signal for the fetus.

24. The method of claim 23, wherein the accelerometer is positioned on the patient based on an intensity of the fetal heart rate signal.

25. The method of claim 21, further including:
sensing a fetal heart rate; and
correlating the sensed fetal movement with the sensed fetal heart rate.

26. The method of claim 21, further comprising:
determining a power spectrum of the signal; and
identifying the signal as a fetal kick when the determined power spectrum is within a predetermined power spectrum range corresponding to a fetal kick.

27. The method of claim 21, further comprising:
determining a periodicity of the signal; and
validating an identified signal as a fetal kick based on the determined periodicity.

28. The method of claim 21, further including determining whether the signal corresponds to a fetal kick based on one or more predetermined rules.

29. The method of claim 28, further including:
learning fetal movement patterns; and
determining whether the signal corresponds to a fetal kick based on the learned fetal movement patterns.

30. The method of claim 21, further including determining a count value indicative of a number of identified signals as a function of time for a given time interval.

31. The method of claim 30, further including determining a fetal health metric based on the count value.

32. A monitoring apparatus, comprising:
a transducer that senses a physiologic movement indicative of fetal movement within the womb of a human or animal patient and generates signals indicative thereof;
a signal origin determiner that determines origins of the fetal movements in the patient based on the generated signals,
a signal identifier that identifies signals from the generated signals that correspond to a fetal kick, wherein the signal identifier validates an identified signal based on the determined origin; and
a counter that counts the identified signal.

* * * * *